United States Patent [19]
Fram et al.

[11] Patent Number: 5,540,679
[45] Date of Patent: Jul. 30, 1996

[54] DEVICE AND METHOD FOR HEATING TISSUE IN A PATIENT'S BODY

[75] Inventors: Daniel B. Fram; Ellison Berns, both of West Hartford, Conn.; Susan M. Ropiak, Hanscom Air Force Base; Donald S. Rowe, Belmont, both of Mass.

[73] Assignee: Boston Scientific Corporation, Watertown, Mass.

[21] Appl. No.: 270,060

[22] Filed: Jul. 1, 1994

Related U.S. Application Data

[63] Continuation of Ser. No. 957,533, Oct. 5, 1992, abandoned.

[51] Int. Cl.⁶ .................................................. A61B 5/04
[52] U.S. Cl. .............................. 606/27; 606/31; 607/101; 607/102
[58] Field of Search ...................... 607/100–105, 607/115, 116, 122; 606/27–33, 41, 42, 191–194

[56] References Cited

U.S. PATENT DOCUMENTS

| | | | |
|---|---|---|---|
| 3,924,628 | 12/1975 | Droegemueller et al. | 607/105 X |
| 4,641,649 | 2/1987 | Walinsky et al. | 128/642 X |
| 4,648,892 | 3/1987 | Kittrell et al. | 606/15 |
| 4,676,258 | 6/1987 | Inokuchi et al. | 128/401 X |
| 4,955,377 | 9/1990 | Lennox et al. | 128/401 |
| 5,019,075 | 5/1991 | Spears et al. | 606/28 X |
| 5,103,804 | 4/1992 | Abele et al. | 128/401 X |
| 5,106,360 | 4/1992 | Ishiwara et al. | 128/401 X |
| 5,135,494 | 8/1992 | Engelson et al. | 604/99 |
| 5,140,987 | 8/1992 | Schuger et al. | 128/642 |
| 5,195,965 | 3/1993 | Shantha | 607/105 X |

OTHER PUBLICATIONS

McMath et al., "Percutaneous laser balloon coagulation of accessory pathways," *SPIE*, vol. 1425, (1991).
Berns et al., "Feasibility of Radiofrequency–Powered, Thermal Balloon Ablation of Atrioventricular Bypass Tracts Via the Coronary Sinus," *American Heart Association*, Oct. 4, 1991.
Calkins et al., "Diagnosis and Cure of the Wolff–Parkinson––White Syndrome or Paroxysmal Supraventricular Tachycardias During a Single Electrophysiologic Test," *The N.E. Journal of M.*, vol. 324, No. 23, Jun. 6, 1991.
Jackman et al., "Catheter Ablation of Accessory Atrioventricular Pathways (Wolff–Parkinson–White Syndrome) by Radiofrequency Current," *The N.E. Journal of Medicine*, vol. 324, No. 23, 0Jun. 6, 1991.
Schuger et al., "Long–Term Effects of Percutaneous Laser Balloon Ablation from the Canine Coronary Sinus," *Circulation*, vol. 86, No. 3, Sep. 1992.
Schuger et al., "Percutaneous Transcatheter Laser Balloon Ablation from the Canine Coronary Sinus: Implications for the Wolff–Parkinson–White Syndrome," *Lasers in Surgery and Medicine*, vol. 10, No. 2, 1990.

*Primary Examiner*—Michael H. Thaler
*Assistant Examiner*—Michael Peffley
*Attorney, Agent, or Firm*—Fish & Richardson P.C.

[57] ABSTRACT

A balloon catheter is provided that includes a catheter shaft constructed for insertion into a blood vessel, a balloon mounted on the catheter shaft, and a heating device located within the balloon and arranged for heating fluid inside the balloon to permit heating of tissue by thermal conduction from the fluid to the tissue through a wall of the balloon. The balloon catheter is inserted into a blood vessel and the balloon is passed through the right atrium of the heart and into the coronary sinus of the heart. The balloon is inflated with the fluid, and the fluid is heated inside the balloon through use of the heating device, to cause heat to pass from the fluid to surrounding tissue by thermal conduction through the wall of the balloon.

6 Claims, 6 Drawing Sheets

DEVICE AND METHOD FOR HEATING TISSUE IN A PATIENT'S BODY

This is a continuation of application Ser. No. 07/957,533, filed Oct. 5, 1992, now abandoned.

BACKGROUND OF THE INVENTION

This invention relates to balloon catheters and similar devices useful to apply heat within a patient's body.

One specific disorder that can be treated by application of heat inside the body is Wolff-Parkinson-White syndrome. Normally, the walls of the atria and ventricles of the heart are electrically isolated from each other by a fibrous ring structure known as the annulus fibrosis. If one or more abnormal accessory pathways (strips of muscular tissue) connect an atrium and ventricle, irregular electrical activity in the heart may result.

This cardiac rhythm disturbance may be treated by percutaneously inserting a catheter into a blood vessel, routing it into the heart, and placing electrodes, which are mounted on the catheter, in direct contact with the wall of an atrium or ventricle. The electrodes cause radiofrequency electrical current or a pulse of direct current electrical energy to pass directly through the heart tissue to destroy the anomalous electrical pathways. If the anomalous pathways are located near the right atrium and ventricle, the catheter is inserted into the right side of the heart through the venous system. If the anomalous pathways are located near the left atrium and ventricle, on the other hand, the catheter is inserted into the left side of the heart through the arterial system; in particular, the catheter passes through the aorta, through the valve between the left ventricle and the aorta, and, if necessary, through the valve between the left atrium and the left ventricle.

In another method of treating Wolff-Parkinson-White syndrome a laser balloon catheter is inserted into the right atrium and into the coronary sinus, which extends into the right atrium, the balloon is inflated, and a laser thermally necroses anomalous bypass tracts near the coronary sinus by direct absorption of electromagnetic radiation by the tissue.

SUMMARY OF THE INVENTION

In one aspect, the invention features a method of ablating electrically conductive pathways of a heart. A balloon catheter is provided that includes a catheter shaft constructed for insertion into a blood vessel, a balloon mounted on the catheter shaft, and a heating device located within the balloon and arranged for heating fluid inside the balloon to permit heating of tissue by thermal conduction from the fluid to the tissue through a wall of the balloon. The balloon catheter is inserted into a blood vessel and the balloon is passed through the right atrium of the heart and into the coronary sinus of the heart. The balloon is inflated with the fluid, and the fluid is heated inside the balloon through use of the heating device, to cause heat to pass from the fluid to surrounding tissue by thermal conduction through the wall of the balloon.

Another aspect of the invention features a cardiac ablation catheter having a distal portion sized to enter the coronary sinus of a heart from the right atrium and constructed and arranged to ablate electrically conductive pathways of the heart while the distal portion of the cardiac ablation catheter is positioned within the coronary sinus. The catheter shaft is constructed for insertion into a blood vessel. A balloon is mounted on the catheter shaft, the catheter shaft and the balloon being sized and constructed to permit the portion of the catheter shaft on which the balloon is mounted to be inserted into the coronary sinus and to permit the balloon to be filled with a fluid inside the coronary sinus. A heating device is located within the balloon for causing tissue to be heated when the balloon is in contact with surrounding tissue. The balloon is constructed to be sufficiently deformable under stress to ensure that when the balloon is inserted into the coronary sinus and is inflated to an inflation pressure that is insufficient to cause substantial dilatation of any portion of the coronary sinus contacted by the balloon, the balloon will conform to the wall of the coronary sinus over the entire wall-facing circumference of the balloon at each point along the length of the balloon even if the coronary sinus has a diameter ratio over the length of the balloon exceeding 1.5 to 1.

In another aspect of the invention the balloon includes a membrane of silicone rubber to ensure that the balloon is highly deformable under stress.

In another aspect of the invention the balloon has a compliance such that the volume of the balloon exhibits at least a one-fold increase when the pressure within the balloon is increased by one-fold starting at a gauge pressure of one-half atmosphere.

The invention achieves the advantages of routing the catheter through the venous system and into the coronary sinus, rather than routing it into the arterial system (reduced risk of serious complications such as valvular damage, cardiac perforation, and cerebral vascular accidents; reduced technical difficulty and time required for the procedure), but further achieves the advantage of achieving a predictable area of thermal damage because the silicone rubber balloon is sufficiently deformable under stress to conform to the irregular shape of the coronary sinus wall when inflated below dilatation pressures. The size of the lesion can be controlled relatively easily because the length of the balloon can be easily controlled by increasing or decreasing the pressure inside the deformable balloon.

Moreover, by using thermal conduction heating to necrose this cardiac tissue, rather than direct passage of electrical or radiative energy through the tissue, the invention makes it easy to control the extent of tissue necrosis.

Another aspect of the invention features a balloon catheter device for heating tissue that includes a catheter shaft constructed for insertion into a blood vessel, a balloon mounted on the catheter shaft, and a plurality or electrophysiologic mapping electrodes. The catheter shaft and the balloon are constructed to permit the balloon to be filled with a fluid. A heating device is located within the balloon for causing tissue to be heated when the balloon is in contact with surrounding tissue. The electrophysiologic mapping electrodes are mounted on the catheter shaft and arranged to perform electrophysiologic mapping.

By combining together, in a single catheter, electrophysiologic mapping electrodes and a balloon heating device, the invention eliminates the need to exchange one catheter for another after electrophysiologic mapping and has the advantage of making the procedure of treating cardiac tissue less technically cumbersome and improving the ability to position the balloon accurately for heating.

Numerous other features, objects, and advantages of the invention will become apparent from the following detailed description when read in connection with the accompanying drawings.

DETAILED DESCRIPTION

Figure 1:
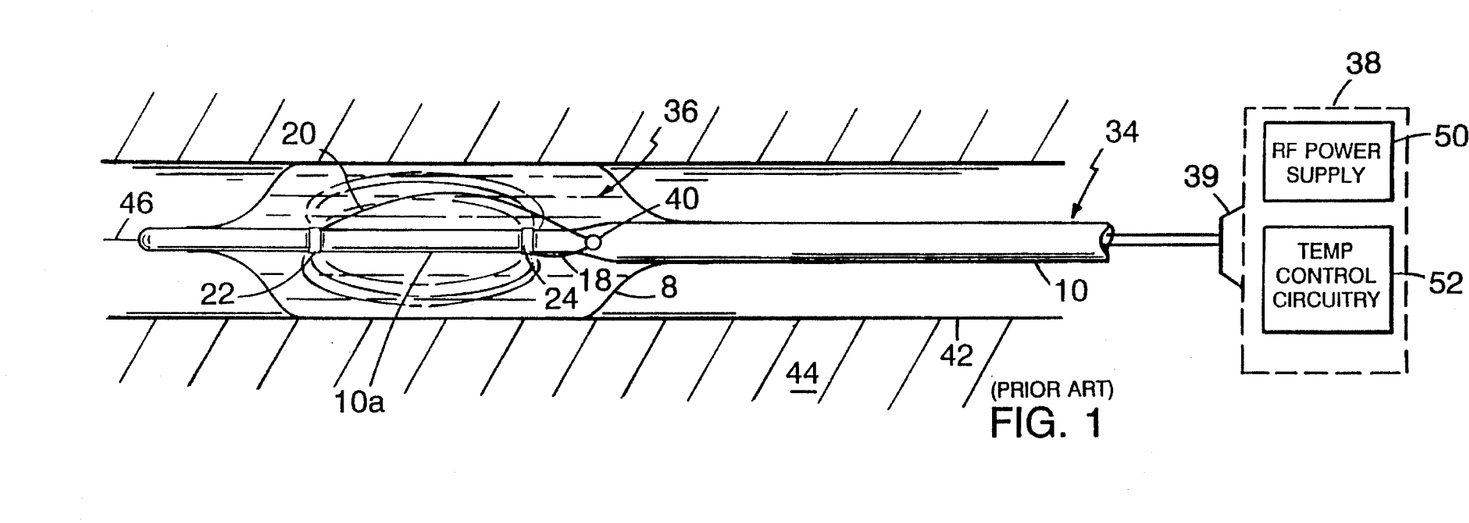
FIG. 1 shows a balloon catheter.

We first explain the structure and operation of various balloon catheter systems known from U.S. Pat. No. 4,955, 377, which is incorporated in its entirety herein by reference.
Structure As shown in FIG. 1, a balloon catheter 34 comprises a polyethylene terephthalate (PET) balloon 8 mounted on nylon catheter shaft 10. The fully extended diameter of balloon 8, when inflated, ranges from 2 millimeters for coronary vascular procedures, to 20 or 35 millimeters for hyperthermia treatment of the prostate, esophagus or colon. The volume of the balloon ranges from ⅛ cc for the smallest balloon to 100 cc for the largest balloon. The wall thickness of balloon 8 is about 0.001 inch. Guidewire 46, which can extend past the distal end of the catheter may be used to guide the catheter through the vascular system or luminal structure. Balloon 8 is fillable with an electrically conductive fluid 36 such as normal saline (0.9 percent NaCl in water), a conductive radiopaque fluid, or a mixture of saline solution and a radiopaque fluid. The exterior of the balloon is coated with a non-stick coating having a low coefficient of friction, such as silicone or polysiloxane.

Annular electrical contacts 22 and 24 inside of balloon 8 have internal diameters matching the portion 10a of the catheter shaft 10 which they surround and are bonded directly to the catheter shaft. The spacing between the contacts is approximately half the length of the balloon, and the spacing from the respective end of the balloon is approximately one fourth the length of the balloon, so that the balloon will heat evenly. While the dimensions of the contacts vary according to the nature of the medical procedure to be performed, it is preferable that the contacts be in the form of annular thin-wall bands having their axial length and diameter about equal. For the range of uses contemplated, the inner diameter of the smallest contact is about 0.050 inch, and the inner diameter of the largest contact is about 0.120 inch. The contacts present a low profile, having a radial thickness of approximately 0.002 inch. The contacts can be made of any conductive material that is compatible with the conductive solution and the conditions of use, but are preferably of a radiopaque metal such as platinum or tantalum, so that they may serve as radiopaque markers during placement of the catheter. Contacts 22 and 24 are preferably coated with tin, so that they may be soldered by means of tin solder to 34 gauge, multi-filament, copper wires 20 and 18, respectively. These wires, which are TEFLON-insulated, and have outer diameters of 0.012 inch, connect contacts 22 and 24, respectively, to opposite poles of current-controlled (constant current) radio-frequency power supply 50. Wires 20 and 18 are enclosed within catheter shaft 10 along its length, and exit catheter shaft 10 through lumen 40, which is located inside of balloon 8.

RF power supply 50 preferably operates at 650 kilohertz, but can be at any frequency within the range of about 100 kilohertz to 1 megahertz. It is important to use radio frequency power rather than direct or low frequency current, or microwave power, because the risk of a physiological response or electrocution response is reduced at RF frequencies above 100 kHz kilohertz as compared with d.c. or low frequencies, and because microwave power would lead to radiative losses in wires 18 and 20, that can result, e.g. in unwanted heating of catheter shaft 10. The fluid 36, while selected to have resistive losses, has an electrical impudence low enough that it will conduct the current supplied by RF power supply 50 at voltages of about 100 volts or lower, so that there will be no arcing across insulated wires 18 and 20. For example, if the current I is set at 1 amp, and the impedance R between the electrodes, through the fluid is 100 ohms, the voltage V will be 100 volts according to V=IR, and the power P dissipated into the fluid will be 100 watts, according to $P=I_2R$. In general, where two electrodes are employed, the impedance between the electrodes will be less than 1000 ohms, preferably in the range of 50 to 500 ohms, and most preferably at about 100 ohms.

In all events the shape of the balloon and the construction and spacing of the electrical contacts are preselected so that the electrical current is substantially confined to the interior of the balloon.

Catheter 34 plugs into RF power supply and temperature control circuitry 38 by means of a plug 39, that is keyed with respect to the particular size of balloon catheter it is associated with, to cause the power supply to operate at a maximum current of ⅒, ¼, ½ or 1 amp. Plug 39 has seven pins, three of which are needed to operate the catheter. During manufacture, a jumper connection is made within plug 39 between a selected two of the remaining four pins. The jumper per connection indicates how much current, at maximum, the RF power supply 50 should produce, depending upon which pins the jumper connection connects. Thus, the user need only select the appropriate catheter 34, and need not be concerned about selecting the appropriate maximum current.

Figure 2:
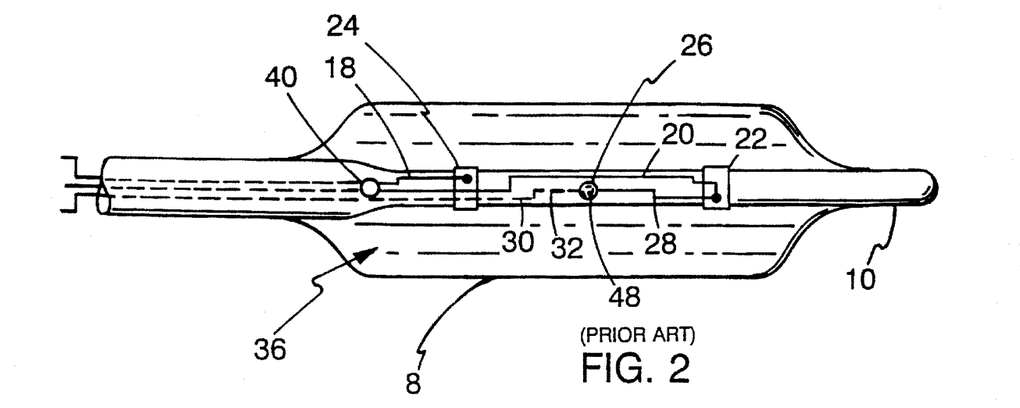
FIG. 2 is a detailed drawing of the balloon portion of the balloon catheter shown in FIG. 1, a temperature sensing device being mounted inside the balloon.

Referring to FIG. 2, in one balloon catheter, a bead thermistor 26, 0.014 inch in diameter and 0.020 inch long, is mounted directly upon catheter shaft 10 between electrodes 22 and 24. Stainless steel thermistor lead 28 connects thermistor 26 with electrode 22. A 34 gauge, multi-filament, TEFLON coated, copper wire 30, outer diameter 0.012 inch, which is soldered to the other stainless steel thermistor lead 32, connects thermistor lead 32 with RF power supply and temperature control circuitry 38 via one of the pins of the plug. Thermistor 26 fits snugly on top of an opening 48 in the wall of catheter shaft 10 midway between electrodes 22 and 24. Wire 30 and thermistor lead 32 are enclosed within catheter shaft 10, and thermistor lead 32 connects with thermistor 26 through opening 48. An insulating coating of epoxy or urethane seals thermistor 26 on top of opening 48, and secures thermistor lead 28 to catheter shaft 10. Alternatively, thermistor lead 28 may be electrically connected to RF power supply and temperature control circuitry 28 in the same manner as thermistor lead 32, rather than being connected to electrode 22.

Figure 3:
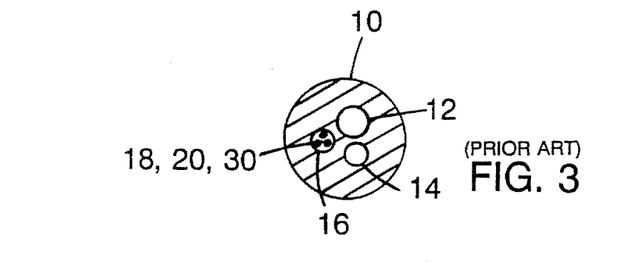
FIG. 3 is a transverse cross-section of the catheter shaft of the balloon catheter shown in FIG. 2.

Referring to FIG. 3, catheter shaft 10 has three lumens 12, 14, and 16. Lumen 12 extends from the proximal end of catheter shaft 10 to the distal end, and provides a conduit for guidewire 46. Lumen 14 extends from the proximal end of the catheter shaft 10 to an outlet in the inside of balloon 8, and provides a conduit for fluid 36 as balloon 8 is inflated and deflated. Lumen 16 extends from the proximal end of catheter shaft 10 to the inside of balloon 8, and provides a conduit for wires 18 and 20, which exit lumen 16 through opening 40 in the wall of catheter shaft 10, and also provides a conduit for wire 30 and thermistor lead 32 through opening 48 in catheter shaft 10, and also provides a conduit for wire 30 and thermistor lead 32 through opening 48 in catheter shaft 10 that is located directly below thermistor 26, as mentioned above.

Figure 4:
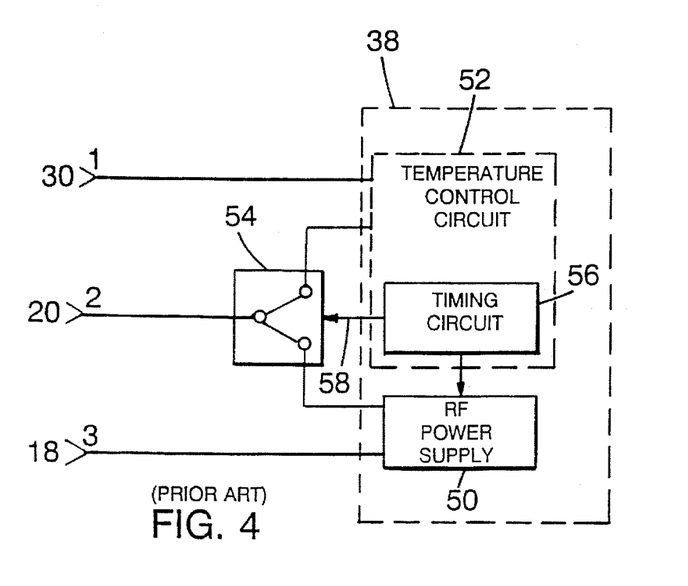
FIG. 4 is a block diagram of the RF power supply and temperature control circuitry for use in conjunction with the balloon catheter of FIG. 2.

Referring to FIG. 4, RF power supply and temperature control circuitry 38 consists of RF power supply 50, temperature control circuit 52, and solid state switch 54. Wire 18 connects electrode 24 with RF power supply 50, and wire 30 connects thermistor 26 with temperature control circuit 52. Timing circuit 56 of temperature control circuit 52 toggles hold/NOT sample line 58 so that solid state switch 54 toggles back and forth, whereby wire 20 functions alternately as a lead connecting RF power supply 50 with electrode 22 and as a lead connecting temperature control circuit 52 with thermistor 26. (Recall that electrode 22 and thermistor 26 are connected by wire 28.) The temperature sensing period is 1 percent of the 60 hertz cycle. When solid state switch 54 connects wire 20 with temperature control circuit 52, temperature control circuit 52 determines how much power, at maximum, RF power supply 50 should supply when solid state switch 54 next connects wire 20 with RF power supply 50. By thus multiplexing between temperature sensing and application of current to the electrodes, the temperature control circuitry eliminates the possibility that thermistor 26 will pick up RF noise from the electrodes 22 and 24.

Figure 5:
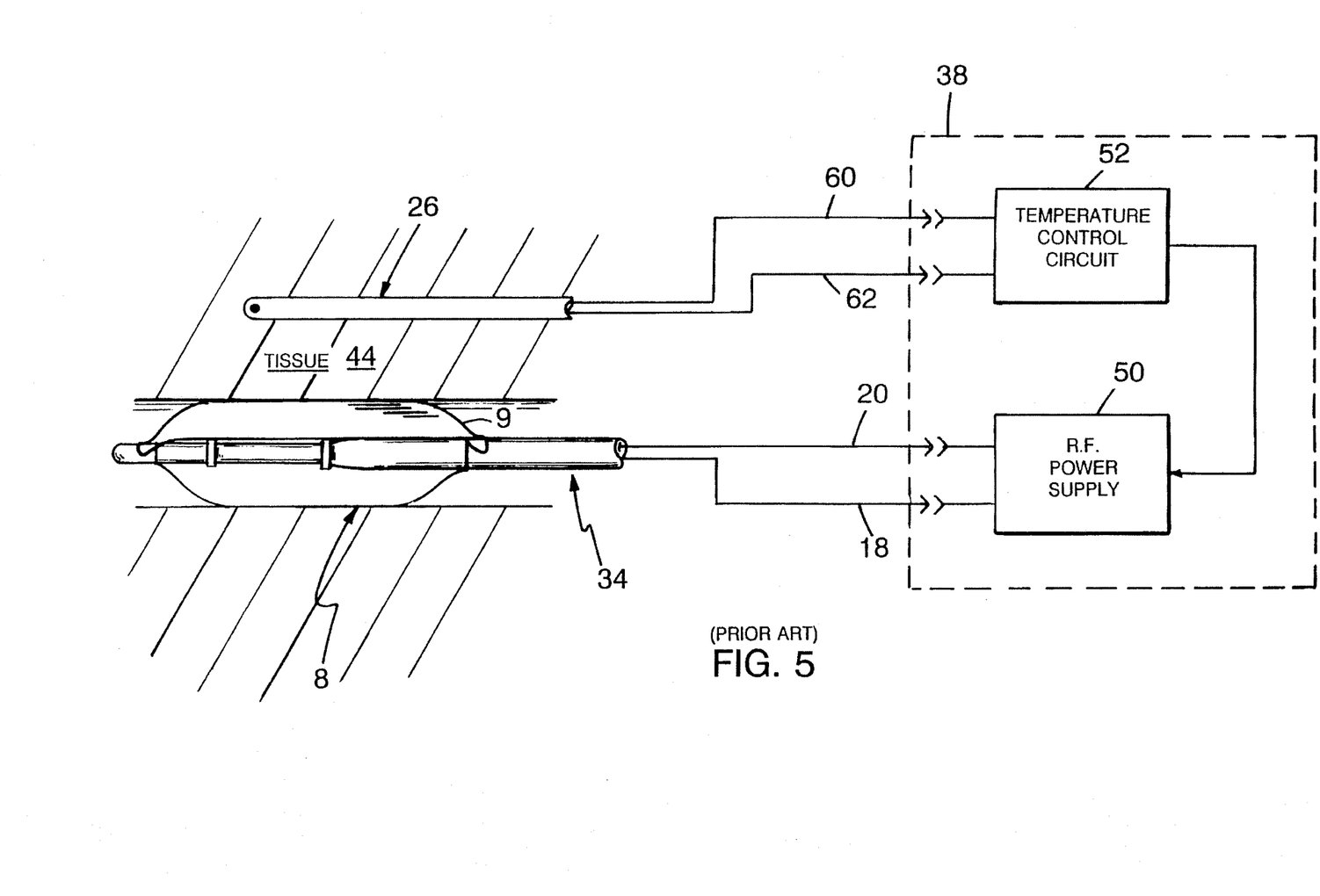
FIG. 5 is a block diagram of the RF power supply and temperature control circuitry for use in conjunction with a balloon catheter system in which a temperature sensor is placed in direct contact with the tissue surrounding the balloon.

Referring to FIG. 5, another balloon catheter system is shown in which temperature sensor 26 is placed in direct contact with tissue 44, outside of balloon catheter 34. Wires 60 and 62 connect temperature sensor 26 with temperature control circuit 52, and wires 20 and 18 connect electrodes 22 and 24 respectively with RF power supply 50. Temperature control circuit 52 regulates RF power supply 50 in response to the input from temperature sensor 26.

Figure 6:
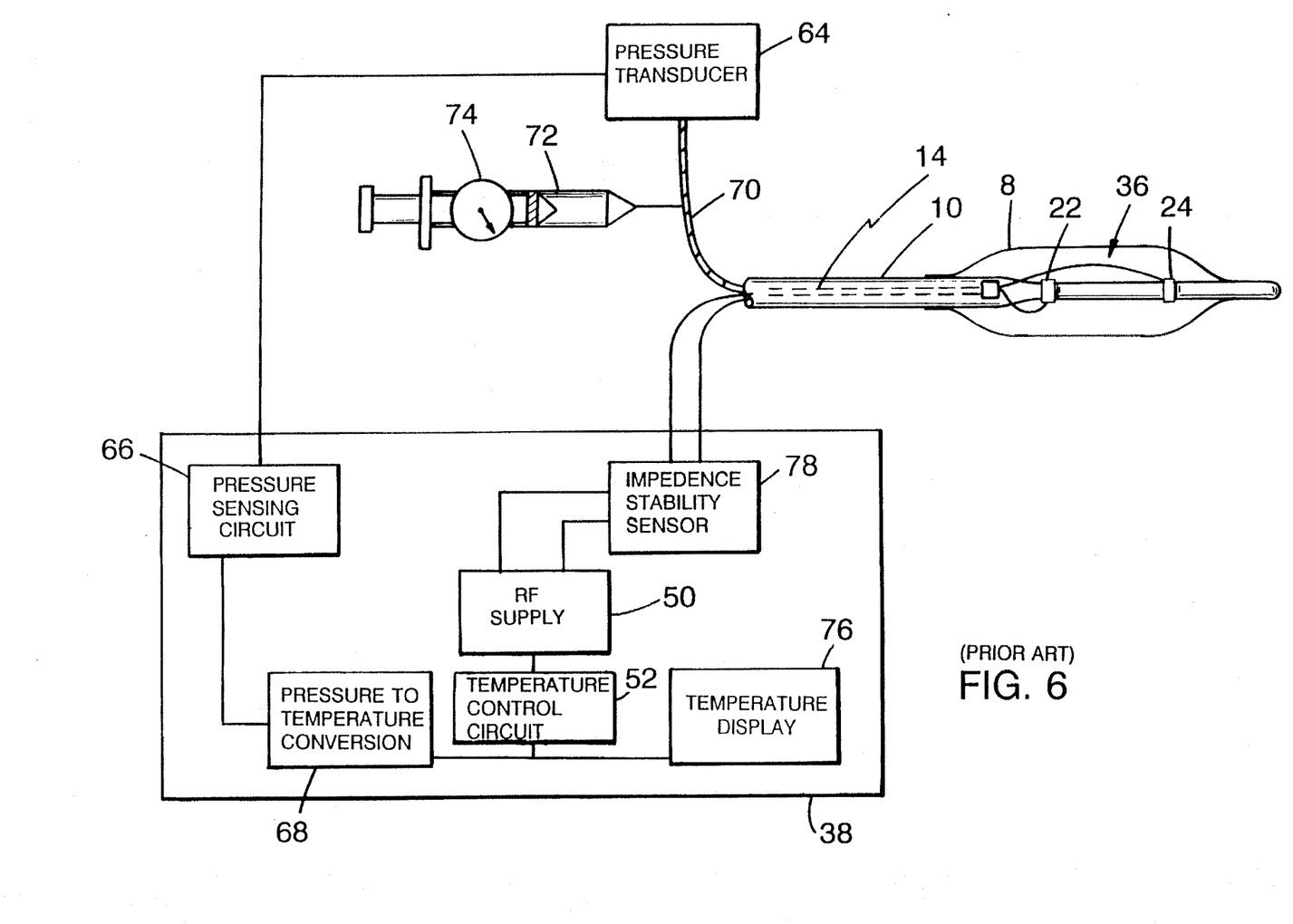
FIG. 6 is a block diagram of the RF power supply and temperature control circuitry for use in conjunction with a balloon catheter system in which a pressure transducer is used inside of the balloon as a means of indirectly measuring the amount of heating of surrounding tissue.

Referring to FIG. 6, another balloon catheter system is shown in which the temperature sensor consists of a pressure transducer 64 in conjunction with pressure sensing circuit 66 and pressure-to-temperature conversion circuit 68. Electrodes 22 and 24 are small enough that the electric current density in the immediate vicinity of the electrodes can induce localized boiling, which aids in the convection of heat from the electrodes to the surrounding tissue 44. The balloon material is heat-set at a temperature in excess of 100° Celsius, so that the balloon material remains dimensionally stable when the fluid 36 within the balloon 8 boils at about 100° Celsius. A flexible tube 70 provides a conduit for fluid into lumen 14 of catheter shaft 10. Inflator 72 is used to inject fluid into flexible tube 70 until a desired pressure is obtained, as indicated by pressure gauge 74. When RF power supply 50 is activated, the high electric field density in the immediate vicinity of each of the electrodes 22, 24 can induce localized boiling of fluid 36. As the fluid 36 heats up, the boiling increases in intensity. The boiling causes the pressure inside balloon 8 to increase. The increase in pressure is measured by pressure transducer 64, as an indirect indication of the amount of heating of the fluid 36, according to phase change pressure/temperature relationships. Temperature control circuit 52 regulates RF power supply 50 in response to the input obtained from pressure-to-temperature conversion circuit 68. Temperature display circuit 76 displays the temperature obtained from pressure-to-temperature conversion circuit 68. Impedance stability sensor 78 detects the initiation of boiling by sensing the instability of catheter impedance due to the formation of vapor at the surfaces of electrodes 22 and 24.

Figure 7:
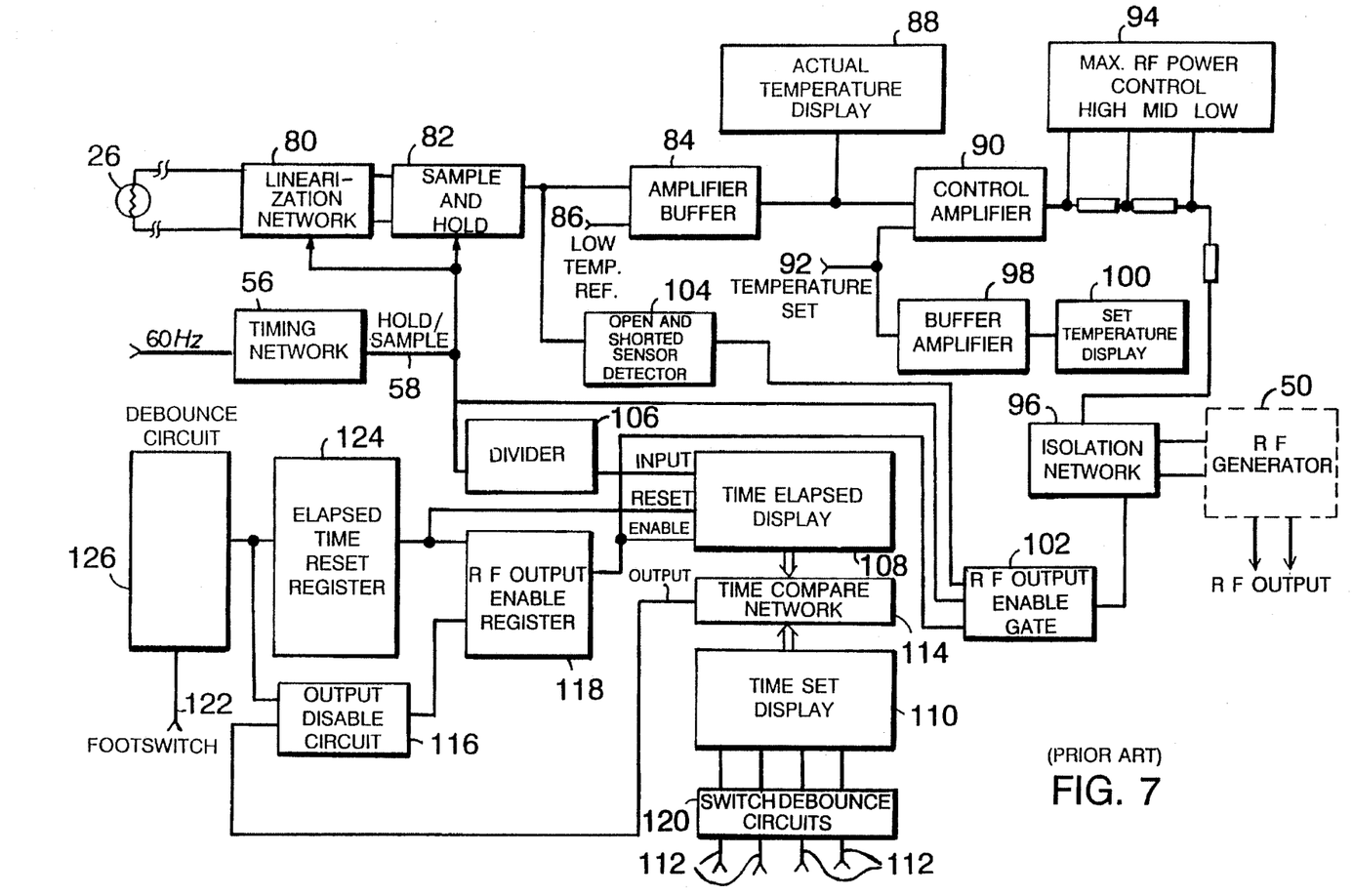
FIG. 7 is a detailed block diagram of the temperature control circuit shown in FIGS. 4, 5 and 6.

Referring to FIG. 7, in temperature control circuit 52, linearization network 80 linearizes the input signal from temperature sensor 26 and delivers the linearized signal to sample and hold register 82. The signal is delivered to amplifier buffer 84 having low-temperature reference 86. Actual temperature display circuit 88 displays the output of amplifier buffer 84. Control amplifier 90 compares the output of amplifier buffer 84 with a temperature set voltage 92 that is set by the user. The maximum RF power control circuit 94 receives the output of control amplifier 90 and determines the level of RF power, at maximum, that the RF power supply 50 should produce. The signal from the maximum RF power control circuit 94 is received by isolation network 96, which interfaces with RF power supply 50. The temperature set voltage 92 is received by buffer amplifier 98 and displayed by set temperature display 100.

Timing circuit 56 toggles hold/NOT sample line 58 at 60 hertz, so that hold/NOT sample line 58 is low during 1 percent of the cycle and high during the other 99 percent of the cycle. Hold/NOT sample line 58 is low when signals from temperature sensor 26 are being sampled and high when signals from temperature sensor 26 are not being sampled. Hold/NOT sample line 58 is received by RF output enable gate 102. The output of sample and hold register 82 is processed by open and short sensor detector 104 to determine whether a sensor malfunction, such as a shorted or open sensor, has occurred. The output of open and shorted sensor detector 104 is received by RF output enable gate 102. RF output enable gate 102 delivers a signal to isolation network 96, which turns off RF power supply 50 when there has been a sensor malfunction or when signals from temperature sensor 26 are being sampled.

Divider 106 receives hold/NOT sample line 58 and delivers its output to time elapsed display 108. Time set display 110 displays the time indicated by time set switches 112, which are set by the user. Time compare network 114 compares the elapsed time with the time set by the user, and delivers an output signal to output disable circuit 116. The output of output disable circuit 116, which is active only when the elapsed time is less than the time set by the user, is delivered to RF output enable register 118. RF output enable register 118 in turn delivers the signal to the enable input to time elapsed display 108, and also to RF output enable gate 102, so that RF power supply 50 may be turned off when the time set by the user has elapsed. Switch debounce circuits 120 are provided for time set switches 112.

The user must depress footswitch 122 in order for RF power supply 50 to operate. While footswitch 122 is activated, and while the elapsed time is less than the time set by the user, output disable circuit 116 delivers a signal to RF output enable register 118, which in turn delivers the signal to the enable input of time elapsed display 108, and also to RF output enable gate 102 so that RF power supply 50 may be turned on. Deactivation of footswitch 122 causes a signal to pass through elapsed time reset register 124, in order to reset time elapsed display 108 and in order to reset RF output enable register 118. The resetting of RF output enable register 118 causes RF output enable gate 102 to turn off RF power supply 50. Debounce circuit 126 is provided for footswitch 122.

Operation

Referring to FIG. 1, balloon catheter 34 may be used as a heat source during or after angioplasty to seal the splitting of the intimal layers of the wall of blood vessel 42 that occurs during angioplasty, and to mold the vessel wall. The blood vessel may be a coronary artery, or a peripheral artery such as an iliac, femoral, renal, carotid, or popliteal artery. The use first preselects the desired therapeutic temperature (temperature set voltage 92, FIG. 7), and sets the length of time for which balloon 8 is to be heated (time set switches 112, FIG. 6). A percutaneous insertion is made with a needle, and guide wire 46 is introduced into the blood vessel 42. Balloon catheter 34 follows the wire. If balloon 8 contains conductive radiopaque fluid, the location of balloon 8 can be monitored by means of fluoroscopy. Balloon 8 is inflated through lumen 14 with either saline, a conductive radiopaque fluid, or a mixture of saline and a radiopaque fluid, to a pressure of 4 to 17 atmospheres, in order to expand the wall of blood vessel 42. The balloon remains inflated for about 20 seconds or longer, depending on the particular blood vessel upon which the angioplasty is being performed. Either during or after the plastic deformation of the vessel wall, with balloon 8 inflated to at least a low level of pressure, the user depresses footswitch 122 (FIG. 7) to initiate the bi-polar heating between the electrodes 36. Heat is dissipated into the fluid according to the formula $P=I^2R$ where P is the power that is dissipated into the fluid, I is the current that is passed through the electrodes, and R is the resistance of the fluid. The heat from the fluid is conducted across the balloon wall into the surrounding tissue 44. For angioplasty procedures, RF power supply 50 supplies a maximum current of ¼ amp and the power dissipated into fluid 36 is about 10 to 25 watts. The fluid will heat to the temperature set by the user, which may be in the range of 45° Celsius to 80° Celsius. Heating will continue until the time set by the user has elapsed, or until the user deactivates footswitch 122.

The balloon catheter may also be used to perform glazing or smoothing of the vessel wall, whereby the balloon 8 is inflated to make light contact with the wall of blood vessel 42, footswitch 122 is activated by the user to initiate heating of the balloon, and the catheter 34 is guided through blood vessel 42 to glaze or smooth the plaque on the vessel wall. The balloon catheter may also be used to dehydrate, compress, and mold plaque to improve patency.

The catheters described above can be used in nonvascular applications such as hyperthermia treatment of benign or malignant tumors, or enlargement of the prostate gland. Hyperthermic effects begin at about 44° Celsius. Heat from balloon 8 destroys the undesired cells, which are eventually absorbed into the patient's body. When a catheters of the type described above are used in such nonvascular applications, the balloon 8 may be large enough that no temperature sensing device is needed, and the fluid 36 can be left to boil off the electrodes without the buildup of excessive pressure within the balloon. The fluid will begin to boil locally in about 5 seconds if the balloon has a diameter of 4 millimeters.

Destruction of Electrically Conductive Pathways in the Heart

Having described various catheters known from U.S. Pat. No. 4,955,377, we now describe apparatus and techniques according to the present invention.

In one embodiment of the invention, a heated balloon catheter is used to treat Wolff-Parkinson-White syndrome by ablating anomalous electrical fibers (i.e., bypass tracts or reentrant circuits) within a heart.

Figure 8:
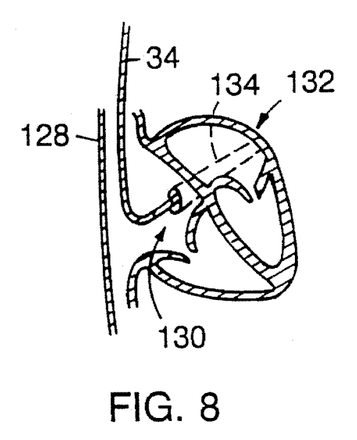
FIG. 8 is a vertical cross-sectional drawing of a heart, illustrating the use of a balloon catheter according to the invention to destroy anomalous electrical fibers in the heart.

With reference to FIG. 8, to treat this type of cardiac rhythm disturbance a catheter 34 of the type described in U.S. Pat. No. 4,955,377 is inserted percutaneously into the venous system and routed through the superior vena cava 128 (or alternatively through the inferior vena cava) into the right atrium 130 of heart 132 and into the coronary sinus 134. (The term "coronary sinus" is used in this application to include not only the coronary sinus proper but also the wider portion of the great cardiac vein, which leads into the coronary sinus.) The fluid within the balloon (not shown) is heated while the balloon is positioned within the coronary sinus, and the heat from the balloon causes necrosis of the tissue surrounding the coronary sinus.

Figure 9:
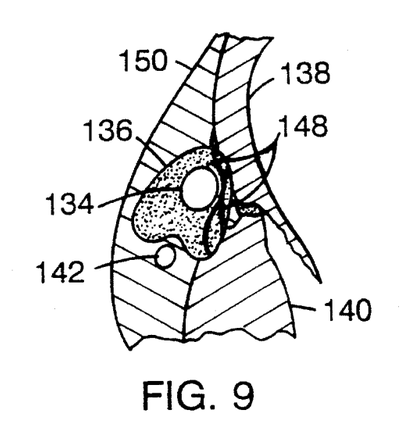
FIG. 9 is a vertical cross-sectional drawing of the back wall of a heart.

The back wall of the heart is shown in vertical cross-section in FIG. 9. Shaded area 136 represents the approximate area of tissue damage surrounding coronary sinus 134. The area of tissue damage, which is located almost entirely within fat pad 150, should include accessory pathways 148, which extend from left atrium wall 138 to left ventricle wall 140, but should not include coronary artery 142.

Figure 10:
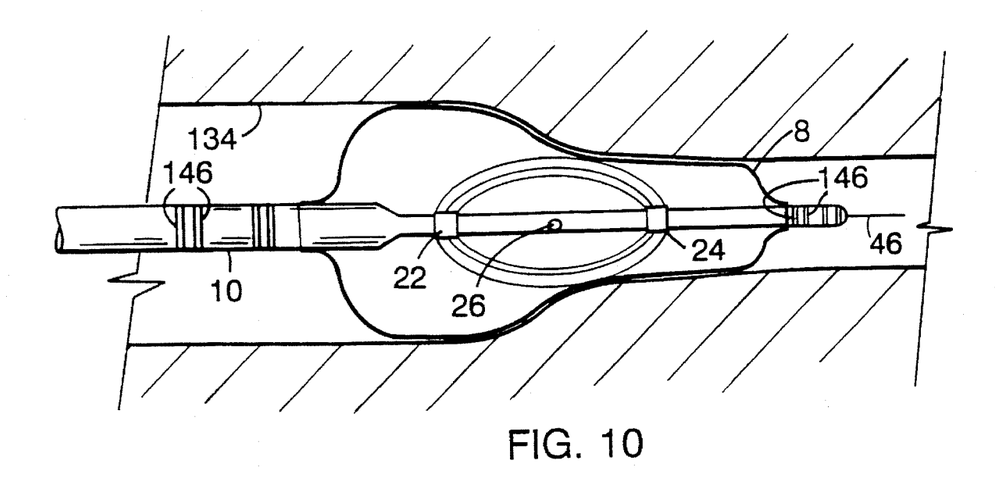
FIG. 10 is drawing showing the balloon portion of a catheter according to the invention with the balloon inflated inside the coronary sinus of a heart.

With reference to FIG. 10, balloon 8 of the catheter constructed for use within coronary sinus 134 is formed of silicone rubber, which is highly deformable under stress to permit balloon 8 to conform to coronary sinus 134 and allow thereby a firm "seal" with the coronary sinus, which tapers sharply and may have a diameter ratio over the length of the balloon exceeding 1.5 to 1. In addition to being highly deformable, silicone rubber has good biocompatibility and ability to maintain strength at high temperature. The silicone rubber balloon is approximately 1.5 centimeters long when uninflated and is expandable to approximately 15 millimeters in diameter. In its uninflated state the silicone rubber balloon is an extruded tube having an inner diameter of 0.60 inches and an outer diameter of 0.80 inches (0.10 inches wall thickness). The extruded tube fits snugly on the larger-diameter portion of catheter shaft 10, and may be attached to catheter shaft 10 by winding a nylon thread around the outside of each end of the extruded tube and applying an adhesive such as cyanoacrylate on top of the thread, or by shrink-fitting rings onto each end of the extruded tube. Other possible balloon materials include latex, urethane, and polyurethane.

The balloon snugly abuts the coronary sinus wall over the entire circumference of the balloon and at each point along the entire length of the balloon (the length of the balloon being one to two centimeters), which is important because the location of damage must be precise in order to destroy a bypass tract effectively. Thus, the use of silicone rubber lends the balloon a very steep compliance (dV/dP) profile: at least a one-fold increase of the volume of the balloon when the pressure within the balloon is increased by one-fold starting at a gauge pressure of one-half atmosphere (i.e., an absolute pressure of one and one-half atmospheres). This high degree of compliance permits a substantial latitude in the direction of balloon growth without the exertion of excessive pressure on the coronary sinus wall. As the pressure within the balloon is increased, the balloon expands, in general, in the direction of least resistance; i.e., the balloon lengthens instead of increasing the pressure on the coronary sinus wall. This feature is important because if blood is allowed to flow between the coronary sinus and the balloon, convective heat loss will prevent the tissue from heating.

The size of the lesion can be controlled by increasing or decreasing the pressure inside the balloon to change the balloon length or by repositioning the balloon.

The tapered portion of catheter shaft 10 may have a diameter of, e.g., 4 French and the wider portion of the catheter shaft may have a diameter of 5.8 French. The catheter shaft preferably has considerable stiffness to give the catheter good axial strength and "push."

In one embodiment pairs of annular electrophysiologic mapping electrodes 146 are provided on catheter shaft 10 to permit electrophysiologic mapping immediately prior to heating, thus eliminating the need to exchange one catheter for another after electrophysiologic mapping. This embodiment has the advantage of making the procedure less technically cumbersome and improving the ability to position the balloon accurately for heating. Each electrophysiologic mapping electrode 146 is electrically connected to a respective conductor that extends through the same lumen that contains the conductors for electrodes 22 and 24. In one embodiment one or more pairs of electrophysiologic mapping electrodes 146 are provided proximal to balloon 8 and one or more pairs are provided distal to the balloon, as shown. Each electrophysiological mapping electrode 146 is one to two millimeters wide and the two electrodes in each pair are separated by one millimeter. There is a distance of five millimeters between each pair. In alternative embodiments the electrophysiologic mapping electrodes may all be located on the same side of the balloon, or even on the balloon itself.

It is believed that the optimal duration of heating for destruction of anomalous electrical fibers is approximately 30 to 60 seconds and that the optimal temperature is approximately 70 to 80 degrees Celsius.

It is anticipated that the invention will be useful not only in treating patients with evident accessory conduction pathways but also in treating patients with atrial flutter and AV node re-entry conditions. To treat these conditions balloon 8 should ordinarily be placed at the mouth of coronary sinus 134 leading into right atrium 130. Consequently, the structure of balloon 8 is somewhat different from the structure of a balloon for use in narrower portions of coronary sinus 134 (e.g., the balloon may be larger or may taper in its uninflated state), and it is even possible to place two balloons on the catheter shaft.

There has been described novel and improved apparatus and techniques for heating tissue in a patient's body. It is evident that those skilled in the art may now make numerous uses and modifications of and departures from the specific embodiment described herein without departing from the inventive concept. Consequently, the invention is to be construed as embracing each and every novel feature and novel combination of features present in or possessed by the apparatus and technique herein disclosed and limited solely by the spirit and scope of the appended claims.

What is claimed is:

1. A method of ablating electrically conductive pathways of a heart, comprising the steps of:

providing a balloon catheter comprising a catheter shaft constructed for insertion into a blood vessel, a balloon mounted on said catheter shaft, and a heating device located within said balloon for heating fluid inside said balloon to permit controlled heating of tissue by thermal conduction from said fluid to said tissue through a wall of said balloon, said balloon having a compliance such that said balloon, when placed within the coronary sinus of said heart and inflated, is conformable to the wall of said coronary sinus over the entire wall-facing circumference of said balloon at each point along the length of said balloon without substantially dilating any portion of said coronary sinus contacted by said balloon, even when said balloon, inflated within said coronary sinus, has a diameter ratio over the length of said balloon exceeding 1.5 to 1, inserting said balloon catheter into a blood vessel and causing said balloon to pass through the right atrium of said heart and into the coronary sinus of said heart, selecting an inflated length of said balloon so as to enable said balloon to create a lesion having a size suitable for ablation of said electrically conductive pathways, and selecting an inflation pressure that will cause said balloon, when inflated with said fluid to said inflation pressure, to have said inflated length, inflating said balloon with said fluid to said inflation pressure, said balloon conforming to the wall of said coronary sinus over the entire wall-facing circumference of said balloon at each point along the length of said balloon without substantially dilating any portion of said coronary sinus contacted by said balloon, said balloon, when inflated within said coronary sinus, having a diameter ratio over the length of said balloon exceeding 1.5 to 1, and causing tissue necrosis while controlling the extent thereof, by heating said fluid inside said balloon through use of said heating device, to cause heat to pass from said fluid to surrounding tissue by thermal conduction through said wall of said balloon, said thermal conduction through said wall of said balloon resulting in said tissue necrosis.

2. A method in accordance with claim 1, wherein said fluid is heated with an intensity and duration sufficient to cause ablation of anomalous electrical fibers in said heart.

3. A method in accordance with claim 1, further comprising the step of:

performing electrophysiologic mapping by means of a plurality of electrophysiologic mapping electrodes mounted on said catheter shaft, whereby electrophysiologic mapping and heating treatment are performed without exchange of catheter devices.

4. A method in accordance with claim 1, further comprising the step of providing feedback information to assist in control of said heating of tissue.

5. A method of ablating electrically conductive pathways of a heart, comprising the steps of:

providing a balloon catheter comprising a catheter shaft constructed for insertion into a blood vessel, a balloon mounted on said catheter shaft, and a heating device located within said balloon for heating fluid inside said balloon to permit controlled heating of tissue by thermal conduction from said fluid to said tissue through a wall of said balloon, said balloon comprising a membrane of silicone rubber to ensure that said balloon is highly deformable under stress, said balloon having a compliance such that said balloon, when placed within the coronary sinus of said heart and inflated, is conformable to the wall of said coronary sinus without substantially dilating said coronary sinus, inserting said balloon catheter into a blood vessel and causing said balloon to pass through the right atrium of said heart and into the coronary sinus of said heart, selecting an inflated length of said balloon so as to enable said balloon to create a lesion having a size suitable for ablation of said electrically conductive pathways, and selecting an inflation pressure that will cause said balloon, when inflated with said fluid to said inflation pressure, to have said inflated length, inflating said balloon with said fluid to said inflation pressure, said balloon conforming to the wall of said coronary sinus without substantially dilating said coronary sinus, and causing tissue necrosis while controlling the extent thereof, by heating said fluid inside said balloon through use of said heating device, to cause heat to pass from said fluid to surrounding tissue by thermal conduction through said wall of said balloon, said thermal conduction through said wall of said balloon resulting in said tissue necrosis.

6. A method of ablating electrically conductive pathways of a heart, comprising the steps of:

providing a balloon catheter comprising a catheter shaft constructed for insertion into a blood vessel, a balloon mounted on said catheter shaft, and a heating device located within said balloon for heating fluid inside said balloon to permit controlled heating of tissue by thermal conduction from said fluid to said tissue through a wall of said balloon, said balloon having a compliance such that the volume of said balloon exhibits at least a one-fold increase when the pressure within said balloon is increased by one-fold starting at a gauge pressure of one-half atmosphere, said compliance being such that said balloon, when placed within the coronary sinus of said heart and inflated, is conformable to the wall of said coronary sinus without substantially dilating said coronary sinus, inserting said balloon catheter into a blood vessel and causing said balloon to pass through the right atrium of said heart and into the coronary sinus of said heart, selecting an inflated length of said balloon so as to enable said balloon to create a lesion having a size suitable for ablation of said electrically conductive pathways, and selecting an inflation pressure that will cause said balloon, when inflated with said fluid to said inflation pressure, to have said inflated length, inflating said balloon with said fluid to said inflation pressure, said balloon conforming to the wall of said coronary sinus without substantially dilating said coronary sinus, and causing tissue necrosis while controlling the extent thereof, by heating said fluid inside said balloon through use of said heating device, to cause heat to pass from said fluid to surrounding tissue by thermal conduction through said wall of said balloon, said thermal conduction through said wall of said balloon resulting in said tissue necrosis.

* * * * *